United States Patent
Schleifenbaum et al.

(10) Patent No.: US 6,902,751 B1
(45) Date of Patent: Jun. 7, 2005

(54) ENCAPSULATED FLAVORINGS

(75) Inventors: Birgit Schleifenbaum, Höxter (DE); Jens Uhlemann, Holzminden (DE); Karl-Heinz Renz, Holzminden (DE)

(73) Assignee: Symrise GmbH & Co. KG, Holzminden (DE)

(*) Notice: Subject to any disclaimer, the term of this patent is extended or adjusted under 35 U.S.C. 154(b) by 0 days.

(21) Appl. No.: 09/707,270

(22) Filed: Nov. 6, 2000

(30) Foreign Application Priority Data

Nov. 12, 1999 (DE) .......................... 199 54 528

(51) Int. Cl.$^7$ ................................. A23L 1/22
(52) U.S. Cl. ..................... 426/89; 426/96; 426/650; 426/651
(58) Field of Search .................. 426/96, 89, 651, 426/650

(56) References Cited

U.S. PATENT DOCUMENTS

| | | | |
|---|---|---|---|
| 2,809,895 A | 10/1957 | Swisher | 99/140 |
| 3,041,180 A | 6/1962 | Swisher | 99/140 |
| 3,704,137 A | 11/1972 | Beck | 99/140 R |
| 3,922,354 A | * 11/1975 | Galluzzi et al. | 426/96 |
| 4,499,112 A | 2/1985 | Miller et al. | 426/276 |
| 4,707,367 A | 11/1987 | Miller et al. | 426/96 |
| 4,820,534 A | 4/1989 | Saleeb et al. | 426/96 |
| 5,009,900 A | 4/1991 | Levine et al. | 426/96 |
| 5,087,461 A | 2/1992 | Levine et al. | 426/96 |
| 5,577,668 A | 11/1996 | King et al. | 239/559 |
| 5,601,865 A | 2/1997 | Fulger et al. | 426/650 |
| 5,603,971 A | 2/1997 | Porzio et al. | 426/96 |
| 5,786,017 A | 7/1998 | Blake et al. | 426/534 |
| 5,792,505 A | 8/1998 | Fulger et al. | 426/650 |
| 5,897,897 A | 4/1999 | Porzio et al. | 426/96 |
| 5,958,502 A | 9/1999 | Fulger et al. | 426/650 |
| 6,096,363 A | * 8/2000 | Van Lengerich | 426/96 |

FOREIGN PATENT DOCUMENTS

| | | |
|---|---|---|
| EP | 673 605 | 9/1995 |
| GB | 1376870 | 12/1974 |

* cited by examiner

*Primary Examiner*—Lien Tran
(74) *Attorney, Agent, or Firm*—Pendorf & Cutliff

(57) ABSTRACT

A method for producing carbohydrate-encapsulated flavorings whose surface has been treated with an inert gas, as well as carbo-hydrate-encapsulated flavorings and the use thereof in food products, consumer articles and pharmaceuticals.

4 Claims, No Drawings

ENCAPSULATED FLAVORINGS

FIELD OF THE INVENTION

The invention relates to a method of producing flavoring-containing particles as well as flavoring-containing particles whose surface has been treated with an inert gas. The resultant encapsulated flavorings are used for flavoring food products and pharmaceuticals.

BACKGROUND OF THE INVENTION

Encapsulated flavorings having a particularly long shelf life are produced in the flavoring industry generally by emulsifying the flavoring in molten carbohydrate mixtures with subsequent shaping. Within an extruder for example, an emulsified flavoring is added to the carbohydrate melt and is then extruded through a perforated plate into a previously charged cooled isopropanol bath. U.S. Pat. Nos. 4,707,367; 4,499,112; 3,704,137; 3,041,180; 2,809,895 describe processes of encapsulating flavorings that use such a solvent bath. In the isopropanol bath, the strands are comminuted during the solidification by an agitator to particle sizes between about 0.3 and 1.5 mm. This solvent bath serves to wash the flavoring contents, which adhere to the particle surface of the resultant particles. The encapsulated flavorings are then dried to remove the remaining solvent by centrifugation and gentle vacuum drying.

The sugar residues must be removed by fine filtration from the solvent used for washing. Water and flavoring residues are recovered by distillation, for recycling. Despite these downstream operations, contaminated solvents must be temporarily stored in separate tanks. The entire production process must comply with a high safety standard. The plant must be made explosion-proof and the flexibility with respect to product change is very restricted because of the problems of contamination.

Disadvantages of these solvent bath processes are due to the complex solvent treatment. Additionally problematic, the resulting particles have a low glass transition temperature and therefore readily form lumps.

By using an extruder and solidification in air, shaped strands can also be produced without using a solvent. This procedure is disclosed in U.S. Pat. Nos. 5,603,971; 5,601,865; 5,087,461; 5,786,017; 5,009,900; 4,820,534 and European Patents WO 94/06308; WO 94/23593. Shaped strands are cooled via a cooling belt or the like. The comminution must be carried out in a downstream mechanical comminution process such as a pelletizer or crusher. During the comminution to the desired particle size between about 0.3 and 1.5 mm, the surface structure of the particles is damaged or destroyed. As a result of mechanical comminution, the surface of the encapsulated particles exposes the flavorings. An increased loading with surface flavorings is disadvantageously connected with this. In addition, an undesirably high fine dust content is formed.

The exposed flavoring on the surface of the particles forms an oily layer on the surface of the particle. This oily layer on the surface causes a marked impairment in the shelf life of the particles.

Therefore, a method to produce flavorings encapsulated in carbohydrates is sought. There is a need for a solvent-free continuous procedure, which involves the integration of the individual steps shaping, cooling, comminution, and dedusting. The particles produced by this sought method must be free from an oily layer from the flavoring used and have a high glass transition temperature. It is desirable for the resulting encapsulated flavorings to have a long shelf life and a high glass transition temperature.

SUMMARY OF THE INVENTION

A process is now provided by the present invention for producing carbohydrate-encapsulated flavorings, produced by emulsifying the flavoring into a carbohydrate melt and producing particles from the resultant melt, which is characterized in that the particles are treated with an inert gas.

The present invention also relates to carbohydrate-encapsulated flavoring particles, produced by emulsifying the flavoring into a carbohydrate melt, characterized in that the particles are treated with an inert gas.

The novel flavoring particles of the present invention are virtually free at the surface from an oily layer from the flavoring used and have a high glass transition temperature.

DETAILED DESCRIPTION OF THE INVENTION

A process is now provided by the present invention for producing carbohydrate-encapsulated flavorings, produced by emulsifying the flavoring into a carbohydrate melt and producing particles from the resultant melt, which is characterized in that the particles are treated with an inert gas.

The process of the present invention can be carried out either batchwise or continuously.

Inert gases for the process of the present invention are nitrogen, noble gases such as helium and argon, and air. The preferred inert gas is air.

The process of the present invention is generally carried out in the temperature range from 10 to 35° C., preferably 20 to 25° C.

The particles are treated with the gas stream by passing the inert gas through a convective dryer at a gas velocity of 0.2 to 4 m/s, preferably 0.5 to 2 m/s.

Convective dryers, for example fluidized-bed apparatuses, are used to remove the surface flavorings the carbohydrate-encapsulated flavoring particles.

The present invention also relates to carbohydrate-encapsulated flavoring particles, produced by emulsifying the flavoring into a carbohydrate melt, characterized in that the particles are treated with an inert gas.

The novel flavoring particles of the present invention are virtually free at the surface from an oily layer from the flavoring used and have a high glass transition temperature. The flavoring is located virtually exclusively in the interior of the particles.

Carbohydrates for the flavorings encapsulated according to the present invention include, but are not limited to hydrolyzed starches, mono- and/or disaccharides, such as maltose.

The flavoring particles have a cylindrical or spherical geometry and a narrow particle size profile. They have a diameter of 0.3 to 12 mm, preferably 0.5 to 1.0 mm, and a length of 0.3 to 10 mm, preferably 0.5 to 1 mm.

The particles of the present invention have a flavoring content of 1 to 25% by weight, preferably 3 to 10% by weight based on the entire weight of the particles.

The particles of the present invention have a glass transition temperature in the range from 45 to 75° C., preferably 50 to 60° C. (DSC method, heating rate 20 K/min).

The flavoring particles of the present invention may comprise further substances, for example emulsifiers, colorants and other fillers.

The flavoring particles of the present invention can be used for flavoring food products, for example instant drink powders, tea, soup powders or sauce powders, confectionery products, chewing gum and pharmaceuticals and also consumer items.

The flavoring particles of the present invention can also be used for flavoring consumer items, for example, oral care products (toothpaste, denture cleaning tablets), cosmetic products, soaps, hygiene products, household products.

The flavoring particles of the present invention can also be used for pharmaceuticals, for example, tablets, candies, instant products.

Those skilled in the art could substitute odorants for flavorings according to the invention.

The process of the invention to produce carbohydrate-encapsulated flavoring particles can be carried out in the following steps:

Melt Production

The first steps in the production are:
1) Melt dry mixture: A dry carbohydrate mixture is prepared and melted by heating to 80 to 120° C., preferably to 90 to 100° C., in an extruder. Double-screw extruders having a plurality of temperature zones are preferred.
2) Emulsify flavoring into the dry mixture: The flavoring, which can additionally contain a suitable emulsifier, is added via a pump continuously into the front extruder region at a dosage of 1 to 25, preferably 3 to 10, % by weight, based on the dry mixture. The extruder dyes ensure the emulsification of the flavoring in the melt.

Integration of the Individual Steps Shaping, Cooling and Comminution

To shape the strands downstream of the perforated plate, the melt must be cooled. Concentric impinging of the perforated plate with cold air cools the melt strands. During this, attention must be paid to uniform heating/cooling of the perforated plate. The strands are comminuted while they are still in the solidification phase by dye-phase pelletizing. A gas-tight design of dye-phase pelletizer having rotary blades, for example, comminutes the strands into pellets. Variable rotary speed control of the dye-phase pelletizer adjusts the particle length as a function of solid throughput. The resultant particles have a bulk density of approximately 0.5 kg/l.

Process for Removing the Surface Flavoring

In this process step, the inventive treatment of the particles is performed using an inert gas.

Contacting is effected in convective dryers by blowing, vortexing or mixing. In a fluidized-bed apparatus, a gas throughput is required which is equivalent to a superficial velocity of 0.2 to 4 m/s, preferably 0.5 to 2 m/s, and a flowthrough time in the range from 5 to 120 min, preferably from 20 to 40 min, at a filling level of 0.01 to 0.5 m, preferably 0.05 to 0.2 m.

Integrated Dedusting

When the particles are contacted with inert gas, adhering or newly formed fine dust is entrained by the gas stream. The dust-laden exhaust gas can be conducted via a suitable dedusting system, so that downstream screening of the particles is unnecessary.

A screening product discharge such as a zigzag screen or ascending tube screen can be connected downstream of the convective dryer.

By means of the process of the present invention, encapsulated flavoring particles are obtained having a low surface flavoring loading by the flavoring and a high glass transition temperature.

The invention is explained in greater detail by means of the following examples.

EXAMPLE 1

Production of Lemon Flavoring Particles

Lemon flavoring is incorporated at 5% into a melt of various maltodextrins, disaccharides and an emulsifier in the extruder. Via a 0.5 mm perforated plate, strands are formed which are comminuted by means of dye-phase pelletizing to a length of 0.5 to 1 mm. 1 kg of the particles is then contacted for 60 minutes with air in a fluidized-bed apparatus operated batchwise. To fluidize the bed contents, air is blown in at a superficial velocity of 1.25 m/s. The inlet temperature of the fluidizing gas is 25° C. The temperature of the exhaust gas is 25° C. Dust contents are then removed via a 0.5 mm screen.

EXAMPLE 2

Instant Drink Powder

An instant drink-powder mixture is formulated consisting of 90% by weight of sucrose, 8% by weight of citric acid, 1% by weight of other ingredients (calcium phosphate, ascorbic acid, modified cellulose, dye) and 1% by weight of yellow-colored lemon flavoring particles (diameter 0.4–0.6 mm) which are produced according to the procedure described. The mixture exhibits a particularly long shelf life with respect to flavoring. Because of the oxidation-sensitive lemon flavoring on the surface of the flavoring particles, the production of off-notes (caused by oxidation) is very greatly minimized.

EXAMPLE 3

Bagged Tea

Flavoring of black tea in teabags with 3% by weight of strawberry flavoring particles (diameter 1 mm, length 1–2 mm). During storage of the tea, the flavoring remains encapsulated in the granular matrix, and is not released until the infusion by dissolving the particle matrix in hot water.

EXAMPLE 4

Chewing Gum

Chewing gum mass is admixed with blue-colored peppermint flavoring particles (diameter 0.6 mm, length 0.4 mm) which were produced by the process described by the present invention. The particles generate a special optical effect. The flavoring is released mechanically on chewing.

EXAMPLE 5

Comparison

In the comparison below (Table 1), the flavoring particles of the invention are compared before and after the contact with air. It is shown that solvent-free decrease of the surface flavoring is possible using the process of the invention.

To determine the amount of flavoring on the surface of the resultant particles, the particles are washed with pentane/ether (particles are not dissolved in this process) and the wash liquid is analyzed for flavoring content with a gas chromatograph. The results of this experiment are reported in ppm based on initial weight of granules.

TABLE 1

| | Before air treatment | After air treatment (fluidized bed 40 min, 1.25 m/s, 25° C.) (according to the invention) |
|---|---|---|
| Lemon granules (diameter 1 mm) | 197 ppm | 9 ppm |
| Strawberry granules (diameter 1 mm) | 943 ppm | 4 ppm |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for producing encapsulated flavoring, comprising the steps of emulsifying the flavoring into a carbohydrate melt, wherein said carbohydrate melt is prepared from a carbohydrate mixture melted by heating to 80 to 120° C., to form a resultant melt and producing particles from the resultant melt, wherein the particles are treated with an inert gas at a gas velocity of 0.2 to 4 m/s.

2. A process according to claim 1, wherein said inert gas is air.

3. A process according to claim 1, wherein said particles are treated with an inert gas in the temperature range from 10 to 35° C.

4. A process according to claim 1, wherein said particles are treated in a gas steam at a gas velocity of 0.5 to 2 m/s.

* * * * *